United States Patent [19]

Austel et al.

[11] 4,327,100

[45] Apr. 27, 1982

[54] 2-(ALKOXY-PHENYL)-IMIDAZO(4,5-B)PYRIDINES AND SALTS THEREOF

[75] Inventors: Volkhard Austel; Manfred Reiffen, both of Biberach; Joachim Heider, Warthausen; Willi Diederen, Biberach, all of Fed. Rep. of Germany

[73] Assignee: Boehringer Ingelheim GmbH, Ingelheim am Rhein, Fed. Rep. of Germany

[21] Appl. No.: 163,970

[22] Filed: Jun. 30, 1980

[30] Foreign Application Priority Data

Jul. 11, 1979 [DE] Fed. Rep. of Germany ....... 2927987

[51] Int. Cl.³ .................... A61K 31/44; C07D 471/04
[52] U.S. Cl. .................................. 424/256; 546/118
[58] Field of Search ........................ 546/118; 424/256

[56] References Cited

U.S. PATENT DOCUMENTS 3,985,891 10/1976 Kutter et al. .................. 546/118

FOREIGN PATENT DOCUMENTS 810545  8/1974 Belgium .
2361757 6/1975 Fed. Rep. of Germany .
2604748 8/1976 Fed. Rep. of Germany .
373392  1/1964 Switzerland .

*Primary Examiner*—John M. Ford
*Assistant Examiner*—Natalia Harkaway
*Attorney, Agent, or Firm*—Hammond & Littell, Weissenberger & Muserlian

[57] ABSTRACT

Compounds of the formula

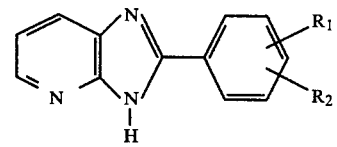

wherein
 $R_1$ is alkoxy of 1 to 3 carbon atoms; and
 $R_2$ is (aralkylsulfinyl of 7 to 9 carbon atoms)-(alkoxy of 2 to 3 carbon atoms); or (unsubstituted, mono-, di- or trisubstituted phenyl-sulfinyl)-(alkoxy of 2 to 3 carbon atoms), where the substituents are attached to the phenyl moiety and are nitro, alkyl of 1 to 3 carbon atoms, alkoxy of 1 to 3 carbon atoms or halogen;

their 3H-tautomers; and non-toxic, pharmacologically acceptable acid addition salts thereof. The compounds are useful as hypertensives and cardiotonics.

9 Claims, No Drawings

2-(ALKOXY-PHENYL)-IMIDAZO(4,5-B)PYRIDINES AND SALTS THEREOF

This invention relates to novel 2-(alkoxy-phenyl)imidazo[4,5-b]pyridines and their non-toxic acid addition salts, to a method of preparing these compounds, to pharmaceutical compositions containing them as active ingredients, and to methods of using them as hypertensives and cardiotonics.

THE PRIOR ART

Belgian Pat. No. 810,545 discloses 2-(alkoxyphenyl)-imidazo[4,5-b]pyridines of the formula

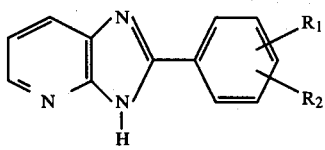

wherein
$R_1$ is alkoxy of 1 to 3 carbon atoms, and
$R_2$ is alkylsulfinyl-(alkoxy of 2 to 3 carbon atoms), their 3H-tautomers, and non-toxic acid addition salts thereof. These compounds are disclosed to possess useful pharmacodynamic properties, especially positive inotropic properties.

DESCRIPTION OF THE INVENTION

We have discovered that certain novel 2-(alkoxyphenyl)-imidazo[4,5-b]pyridines of the formula propoxyphenylsulfinyl, nitrophenylsulfinyl, methyl-nitrophenylsulfinyl, methoxy-nitrophenylsulfinyl, fluorophenylsulfinyl, chlorophenylsulfinyl, bromophenylsulfinyl, difluorophenylsulfinyl, dichlorophenylsulfinyl, dibromophenylsulfinyl, fluoro-chlorophenylsulfinyl, fluoro-bromophenylsulfinyl, chlorobromophenylsulfinyl, methyl-methoxyphenylsulfinyl, methyl-dimethoxyphenylsulfinyl, dimethyl-methoxyphenylsulfinyl, fluoromethoxyphenylsulfinyl, fluoro-dimethoxyphenylsulfinyl, fluoro-methylphenylsulfinyl, chloro-methoxyphenylsulfinyl, bromo-dimethoxyphenylsulfinyl or fluoromethylmethoxy-phenylsulfinyl.

A preferred sub-genus is constituted by those compounds of the formula I wherein
$R_1$ is methoxy, and
$R_2$ is —O—CH$_2$—CH$_2$—X, where X is benzylsulfinyl, phenylsulfinyl, chlorophenylsulfinyl, methylphenylsulfinyl, nitrophenylsulfinyl, methoxyphenylsulfinyl, dimethoxyphenylsulfinyl or dimethoxymethylphenylsulfinyl,
their 3H-tautomers, and non-toxic, pharmacologically acceptable acid addition salts thereof.

An especially preferred sub-genus is constituted by those compounds of the above preferred sub-genus, where $R_1$ is in 4-position and $R_2$ is in 2-position on the phenyl ring.

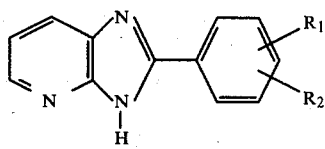

wherein
$R_1$ is alkoxy of 1 to 3 carbon atoms; and
$R_2$ is (aralkylsulfinyl of 7 to 9 carbon atoms)-(alkoxy of 2 to 3 carbon atoms); or (unsubstituted, mono-, di- or trisubstituted phenylsulfinyl)-(alkoxy of 2 to 3 carbon atoms), where the substituents are attached to the phenyl moiety and are nitro, alkyl of 1 to 3 carbon atoms, alkoxy of 1 to 3 carbon atoms or halogen;
their 3H-tautomers; and non-toxic, pharmacologically acceptable acid addition salts thereof have significantly superior pharmacodynamic properties, especially superior hypertensive and/or positive inotropic properties.

Examples of specific embodiments of $R_1$ and $R_2$ in formula I are the following:
$R_1$: Methoxy, ethoxy, propoxy or isopropoxy.
$R_2$: 2-Benzylsulfinylethoxy, 3-benzylsulfinylpropoxy, 2-phenylethylsulfinylethoxy, 3-phenylethylsulfinylpropoxy, 2-phenylpropylsulfinylethoxy, 3-phenylpropylsulfinylpropoxy, or ethoxy or propoxy substituted with phenylsulfinyl, methylphenylsulfinyl, dimethylphenylsulfinyl, trimethylphenylsulfinyl, ethylphenylsulfinyl, isopropylphenylsulfinyl, methoxyphenylsulfinyl, dimethoxyphenylsulfinyl, trimethoxyphenylsulfinyl, diethosyphenylsulfinyl, The compounds embraced by formula I may be prepared by oxidizing an imidazo[4,5-b]pyridine of the formula

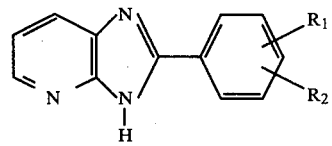

wherein
$R_1$ has the same meanings as in formula I; and
$R_3$ is (aralkylthio of 7 to 9 carbon atoms)-(alkoxy of 2 to 3 carbon atoms); or (unsubstituted, mono-, di- or trisubstituted phenylthio)-(alkoxy of 2 to 3 carbon atoms), where the substituents are nitro, alkyl of 1 to 3 carbon atoms, alkoxy of 1 to 3 carbon atoms or halogen.

The oxidation is advantageously performed in a solvent, such as water, water pyridine, acetone, glacial acetic acid, dilute sulfuric acid or trifluoroacetic acid, and, depending upon the particular oxidizing agent which is used, at temperatures between −80° and +100° C.

The oxidation is preferably carried out with one equivalent of the oxidizing agent, for example with hydrogen peroxide in glacial acetic acid at 0° to 20° C. or in acetone at 0° to 60° C.; with a peracid, such as performic acid, in glacial acetic acid or trifluoroacetic acid at 0° to 50° C.; with sodium metaperiodate in aqueous methanol or ethanol at 15° to 25° C.; with tert. butyl hypochlorite in methanol at −80° to −30° C.; with iodobenzene dichloride in aqueous pyridine at 0° to 50° C.; with nitric acid in glacial acetic acid at 0° to 20° C.; with chromic acid in glacial acid or in acetone at 0° to 20° C.; or with sulfuryl chloride in methylene chloride at −70° C., where the thioether-chloro complex obtained is hydrolyzed in aqueous ethanol.

The compounds embraced by formula I are basic and therefore form addition salts with inorganic or organic acids. Examples of non-toxic, pharmacologically acceptable acid addition salts are those formed with hydrochloric acid, hydrobromic acid, sulfuric acid, phosphoric acid, fumaric acid, succinic acid, tartaric acid, citric acid, lactic acid, maleic acid or the like.

The starting compounds of the formula II may be obtained by reacting a corresponding haloalkoxyimidazo[4,5-b]pyridine (see Belgian Patent 810,545) with a corresponding mercaptan in the presence of a base, such as sodium methylate.

The following examples illustrate the present invention and will enable others skilled in the art to understand it more completely. It should be understood, however, that the invention is not limited solely to the particular examples given below.

EXAMPLE 1

2-[2-(2-Phenylsulfinyl-ethoxy)-4-methoxyphenyl]-imidazo[4,5-b]pyridine

(a)
2-[2-(2-Phenylthio-ethoxy)-4-methoxyphenyl]-imidazo[4,5-b]pyridine

A solution of 2.0 gm (0.036 mol) of sodium methylate in 50 ml of absolute methanol was admixed with 1.85 ml (0.018 mol) of thiophenol and 4.6 gm (0.015 mol) of 2-[2-(2-chloroethoxy)-4-methoxyphenyl]imidazo[4,5-b]pyridine hydrochloride. After refluxing for 4 hours, the reaction mixture was evaporated in vacuo, the residue was dissolved in water/methylene chloride, and the organic phase was separated and dried over magnesium sulfate. A pre-purification was carried out on 50 gm of silicagel with methylene chloride/acetone (100:0 to 80:20). The product was used in the next step without further purification.

Yield: 2.8 gm (50% of theory).

(b)

A solution of 2.8 gm (0.0074 mol) of 2-[2-(2-phenylthioethoxy)-4-methoxyphenyl]imidazo[4,5-b]pyridine in 40 ml of glacial acetic acid was admixed with 0.84 gm of hydrogen peroxide (30%), and the mixture was stirred for 2 hours at room temperature. Subsequently, the reaction mixture was diluted with 20 ml of water, neutralized with potassium carbonate, extracted three times with 50 ml each of methylene chloride, and dried over magnesium sulfate. The purification was carried out on 70 gm of silicagel with methylene chloride/acetone (100:0 to 80:20).

Yield: 2.1 gm (72% of theory).
M.p.: 185°–186° C.

EXAMPLE 2

(a)
2-[2-(2-Benzylthio-ethoxy)-4-methoxyphenyl]-imidazo[4,5-p]-pyridine

This compound was prepared analogous to Example 1(a) from 3.6 gm 2-[2-(2-chloroethoxy)-4-methoxyphenyl]imidazo[4,5-b]pyridine hydrochloride.

Yield 1.8 gm (40% of theory).

(b)
2-[2-(2-Benzylsulfinyl-ethoxy)-4-methoxyphenyl]imidazo[4,5-b]pyridine

This compound was prepared analogous to Example 1(b) from 1.8 gm of 2-[2-(2-benzylthio-ethoxy)-4-methoxyphenyl]imidazo[4,5-b]pyridine.

Yield: 0.9 gm (48% of theory).
M.p.: 193°–194° C.

EXAMPLE 3

(a)
2-{2-[2-(4-chlorophenylthio)-ethoxy]-4-methoxyphenyl}imidazo-[4,5-b]pyridine This compound was prepared analogous to Example 1(a) from 6.1 gm of 2-[2-(2-chloroethoxy)-4-methoxyphenyl]imidazo[4,5-b]pyridine hydrochloride.

Yield: 4.2 gm (51% of theory).

(b)
2-{2-[2-(4-chlorophenylsulfinyl)-ethoxy]-4-methoxyphenyl}imidazo[4,5-b]pyridine This compound was prepared analogous to Example 1(b) from 4.0 gm of 2-{2-[2-(4-chlorophenylthio)-ethoxy]-4-methoxyphenyl}imidazo[4,5-b]pyridine Yield: 2.6 gm (63% of theory).
M.p.: 171°–173° C.

EXAMPLE 4

(a)
2-{2-[2-(4-Methylphenylthio)-ethoxy]-4-methoxyphenyl}imidazo[4,5-b]pyridine This compound was prepared analogous to Example 1(a) from 6.1 gm of 2-[2-(2-chloroethoxy)-4-methoxyphenyl]imidazo[4,5-b]pyridine hydrochloride.

Yield: 1.4 gm (18% of theory).

(b)
2-{2-[2-(4-Methoxyphenylsulfinyl)-ethoxy]-4-methoxyphenyl}imidazo[4,5-b]pyridine This compound was prepared analogous to Example 1(b) from 1.3 gm of 2-{2-[2-(4-methylphenylthio)-ethoxy]-4-methoxyphenyl}imidazo[4,5-b]pyridine.

Yield: 1.0 gm (77% of theory).
M.p.: 76°–120° C.

EXAMPLE 5

(a)
2-{2-[2-(4-Methoxyphenylthio)-ethoxy]-4-methoxyphenyl}imidazo[4,5-b]pyridine This compound was prepared analogous to Example 1(a) from 4.6 gm of 2-[2-(2-chloroethoxy)-4-methoxyphenyl]imidazo[4,5-b]pyridine hydrochloride.

Yield: 4.9 gm (80% of theory).

(b)
2-{2-[2-(4-Methoxyphenylsulfinyl)-ethoxy]-4-methoxyphenyl}imidazo[4,5-b]pyridine This compound was prepared analogous to Example 1(b) from 4.8 gm of 2-{2-[2-(4-methoxyphenylthio)-ethoxy]-4-methoxyphenyl}imidazo[4,5-b]pyridine.

Yield: 1.6 gm (32% of theory).
M.p. 198°–201° C.

EXAMPLE 6

(a)
2-{2-[2-(2-Methoxyphenylthio)-ethoxy]-4-methoxyphenyl}imidazo[4,5-b]pyridine This compound was prepared analogous to Example 1(a) from 4,6 gm of 2-[2-(2-chloroethoxy)-4-methoxyphenyl]imidazo[4,5-b]pyridine hydrochloride.

Yield: 2.3 gm (38% of theory).

(b)
2-{2-[2-(2-Methoxyphenylsulfinyl)-ethoxy]-4-methoxyphenyl}imidazo[4,5-b]pyridine This compound was prepared analogous to Example 1(b) from 2.3 gm of 2-{2-[2-(2-methoxyphenylthio)-ethoxy-4-methoxyphenyl}imidazo[4,5-b]pyridine.
Yield: 1.3 gm (54% of theory).
M.p.: 128°–132° C.

EXAMPLE 7

(a)
2-{2-[2-(3,4-dimethoxyphenylthio)-ethoxy]-4-methoxyphenyl}imidazo[4,5-b]pyridine This compound was prepared analogous to Example 1(a) from 4.6 gm of 2-[2-(2-chloroethoxy)-4-methoxyphenyl]imidazo[4,5-b]pyridine hydrochloride.
Yield: 4.3 gm (65% of theory).

(b)
2-{2-[2-(3,4-dimethoxyphenylsulfinyl)-ethoxy]-4-methoxyphenyl}imidazo[4,5-b]pyridine This compound was prepared analogous to Example 1(b) from 4.2 gm of 2-{2-[2-(3,4-dimethoxyphenylthio)-ethoxy]-4-methoxyphenyl}imidazo[4,5-b]pyridine.
Yield: 2.7 gm (62% of theory).
M.p.: 155°–159° C.

EXAMPLE 8

(a)
2-{2-[2-(2-Methyl-4,5-dimethoxyphenylthio)-ethoxy]-4-methoxyphenyl}imidazo[4,5-b]pyridine.

This compound was prepared analogous to Example 1(a) from 4.6 gm of 2-[2-(2-chloroethoxy)-4-methoxyphenyl]imidazo[4,5-b]-pyridine hydrochloride.
Yield: 3.8 gm (56% of theory).

(b)
2-{2-[2-(2-Methyl-4,5-dimethoxyphenylsulfinyl)-ethoxy]-4-methoxyphenyl}imidazo[4,5-b]pyridine This compound was prepared analogous to Example 1(b) from 3.7 gm of 2-{2-[2-(2-methyl-4,5-dimethoxyphenylthio)-ethoxy]-4-methoxyphenyl}imidazo[4,5-b]pyridine.
Yield: 1.9 gm (51% of theory).
M.p.: 170°–172° C.

EXAMPLE 9

(a)
2-{2-[2-(4-Nitrophenylthio)-ethoxy]-4-methoxyphenyl}imidazo[4,5-b]pyridine This compound was prepared analogous to Example 1(a) from 4.6 gm of 2-[2-(2-chloroethoxy)-4-methoxyphenyl]imidazo[4,5-b]pyridine hydrochloride.
Yield: 3.8 gm (60% of theory).

(b)
2-{2-[2-(4-Nitrophenylsulfinyl)-ethoxy]-4-methoxyphenyl}imidazo[4,5-b]pyridine This compound was prepared analogous to Example 1(b) from 4.7 gm of 2-{2-[2-(4-nitrophenylthio)-ethoxy]-4-methoxyphenyl}imidazo[4,5-b]pyridine.
Yield: 0.94 gm (19% of theory).
M.p.: 202.5°–204.5° C.

Example 10

(a)
2-{2-[2-(2,4-Dimethoxyphenylthio)-ethoxy]-4-methoxyphenyl}imidazo[4,5-p]pyridine This compound was prepared analogous to Example 1(a) from 4.0 gm of 2-[2-(2-chloroethoxy)-4-methoxyphenyl]imidazo[4,5-b]pyridine hydrochloride.
Yield: 4.6 gm (70% of theory).

(b)
2-{2-[2-(2,4-Dimethoxyphenylsulfinyl)-ethoxy]-4-methoxyphenyl}imidazo[4,5-b]pyridine This compound was prepared analogous to Example 1(b) from 2.3 gm of 2-{2-[2-(2,4-dimethoxyphenylthio)-ethoxy]-4-methoxyphenyl}imidazo[4,5-b]pyridine.
Yield: 1.8 gm (78% of theory).
M.p.: 176°–179° C.

As indicated above, the compounds of the present invention, that is, those embraced by formula I above, their 3H-tautomers, and non-toxic, pharmacologically acceptable acid addition salts thereof, have useful pharmacodynamic properties. More particularly, they exhibit hypertensive and positive inotropic activities in warm-blooded animals, such as cats.

The above pharmacological properties of the compounds of this invention were ascertained by the test methods described below, and Tables I and II show the results of these tests for a few representative species of the genus, where A = 2-[2-(2-Phenylsulfinyl-ethoxy)-4-methoxyphenyl]imidazo[4,5-b]pyridine, B = 2-{2-[2-(4-Chlorophenylsulfinyl)-ethoxy]-4-methoxyphenyl}-imidazo-[4,5-b]pyridine C = 2-{2-[2-(4-Methylphenylsulfinyl)-ethoxy]-4-methoxyphenyl}-imidazo[4,5-b]pyridine, D = 2-{2-[2-(2-Methyl-4,5-dimethoxyphenylsulfinyl)-ethoxy]-4-methoxyphenyl}-imidazo[4,5-b]pyridine and E = 2-{2-[2-(4-Nitrophenylsulfinyl)-ethoxy]-4-methoxyphenyl}-imidazo[4,5-b]pyridine.

1. Determination of the effect on blood pressure and of the positive inotropic activity in the anesthetized cat The test was performed on cats which were anesthetized with pentobarbital sodium (40 mg/kg i.p.). The animals breathed spontaneously. The arterial blood pressure was measured in the aorta abdominalis by a Statham pressure transducer (P 23 Dc). The positive inotropic effect was determined by measuring the pressure in the left ventricle by means of a catheter tip manometer (Millar PC 360 A). The contractility parameter $(dp/dt_{max})$ was registered by means of an analog differentiating circuit.

The test compound was injected into the vena femoralis. Physiological sodium chloride solution or polydiol 200 was used as solvent. Each substance was tested in at least 3 cats, dose 2 mg/kg i.v.

The following table shows the average values:

TABLE I

| Compound | Dose mg/kg i. v. | Change in blood pressure mmHg | Increase in dp/dt % |
| --- | --- | --- | --- |
| A | 2.0 | + 33/20 | + 115 |
| B | 2.0 | + 60/42 | + 101 |
| C | 2.0 | + 70/45 | + 96 |
| D | 2.0 | + 13/5 | + 45 |

TABLE I-continued

| Compound | Dose mg/kg i. v. | Change in blood pressure mmHg | Increase in dp/dt % |
|---|---|---|---|
| E | 2.0 | + 67/32 | + 60 |

2. Acute toxicity

The acute toxicity was determined in white mice after oral administration of a single dose of 300 mg/kg (observation time: 14 days).

TABLE II

| Compound | $LD_{50}$ mg/kg p. o. |
|---|---|
| B | > 300 (0 out of 6 animals died) |
| C | > 300 (0 out of 6 animals died) |
| D | > 300 (0 out of 6 animals died) |

Based on their pharmacological properties, the compounds of the formula I, their 3H-tautomers, and their non-toxic, pharmacologically acceptable acid addition salts are suitable for the treatment of chronic cardiac insufficiency and for the treatment of acute cardiac failure in cardiogenic shock.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.36 to 2.86 mgm/kg body weight, preferably 0.71 to 1.43 mgm/kg body weight, 1 to 4 times daily.

The following examples illustrate a few pharmaceutical dosage unit compositions comprising a compound of the present invention as an active ingredient and represent the best modes contemplated of carrying out the invention. The parts are parts by weight unless otherwise specified.

EXAMPLE 11

Tablets

The tablet composition is compounded from the following ingredients:

| | |
|---|---|
| 2-[2-(2-Phenylsulfinyl-ethoxy)-4-methoxyphenyl]-imidazo [4,5-b] pyridine | 100.0 parts |
| Lactose | 50.0 parts |
| Polyvinylpyrrolidone | 5.0 parts |
| Carboxymethyl cellulose | 19.0 parts |
| Magnesium stearate | 1.0 parts |
| Total | 175.0 parts |

Preparation

The active ingredient, the lactose and the carboxymethyl cellulose are intimately admixed with each other, the mixture is moistened with an aqueous solution of the polyvinylpyrrolidone, and the moist mass is granulated by passing it through a 1.5 mm-mesh screen. The granulate is dried at 50° C., passed through a 1 mm-mesh screen, admixed with the magnesium stearate, and the composition is compressed into 175 mgm-tablets. Each tablet is an oral dosage unit composition containing 100 mgm of the active ingredient.

EXAMPLE 12

Coated pills

The pill core composition is compounded from the following ingredients:

| | |
|---|---|
| 2-[2-(Phenylsulfinyl-ethoxy)-4-methoxyphenyl]-imidazo [4,5-b] pyridine | 50.0 parts |
| Corn starch, dry | 20.0 parts |
| Soluble starch | 2.0 parts |
| Carboxymethyl cellulose | 7.0 parts |
| Magnesium stearate | 1.0 parts |
| Total | 80.0 parts |

Preparation

The active ingredient and the corn starch are intimately admixed with each other, the mixture is moistened with an aqueous solution of the soluble starch, and the moist mass is granulated by passing it through a 1.0 mm-mesh screen. The granulate is dried at 50° C., passed through a 1 mm-mesh screen, admixed with the magnesium stearate and the carboxymethyl cellulose, and the composition is compressed into 80 mgm-pill cores which are subsequently coated with a thin-shell consisting essentially of a mixture of sugar and talcum. Each coated pill is an oral dosage unit composition containing 50 mgm of the active ingredient.

EXAMPLE 13

Suppositories

The suppository composition is compounded from the following ingredients:

| | |
|---|---|
| 2-[2-(2-Phenylsulfinyl-ethoxy)-4-methoxyphenyl]-imidazo [4,5-b] pyridine | 75.0 parts |
| Suppository base (e.g. cocoa butter) | 1,625.0 parts |
| Total | 1,700.0 parts |

Preparation

The suppository base is melted and cooled to 38° C., the milled active ingredient is homogeneously dispersed therein, the mixture is cooled to 35° C., and 1.7 gm-portions thereof are poured into cooled suppository molds and allowed to harden therein. Each suppository is a rectal dosage unit composition containing 75 mgm of the active ingredient.

EXAMPLE 14

Hypodermic solution

The solution is compounded from the following ingredients:

| | |
|---|---|
| 2-[2-(2-Phenylsulfinyl-ethoxy)-4-methoxyphenyl]-imidazo-[4,5-b] pyridine | 50.0 parts |
| Sorbitol | 250.0 parts |
| Distilled water q.s.ad | 5000.0 parts by vol. |

Preparation

The active ingredient and the sorbitol are dissolved in a sufficient amount of distilled water, the solution is diluted with additional distilled water to the indicated volume, and the dilute solution is filtered until free from suspended particles. The filtrate is filled into 5 cc ampules which are subsequently sterilized for 20 minutes at 120° C. and sealed. The contents of each ampule are an injectable dosage unit composition containing 50 mgm of the active ingredient.

EXAMPLE 15

Drop solution

The solution is compounded from the following ingredients:

| | | |
|---|---|---|
| 2-[2-(2-Phenylsulfinyl-ethoxy)-4-methoxyphenyl]-imidazo [4,5-b]pyridine | 5.0 | parts |
| Methyl p-hydroxy-benzoate | 0.035 | parts |
| Propyl p-hydroxy-benzoate | 0.015 | parts |
| Oil of anise | 0.05 | parts |
| Menthol | 0.06 | parts |
| Saccharin sodium | 1.0 | parts |
| Glycerine | 10.0 | parts |
| Ethanol | 40.0 | parts |
| Distilled water q.s.ad | 100.0 | parts by vol. |

Preparation

The p-hydroxy-benzoates are dissolved in the ethanol, and the oil of anise and the menthol are added thereto (solution A). The active ingredient, the glycerine and the saccharin sodium are dissolved in the distilled water (solution B). Solutions A and B are combined, and the resulting solution is filtered until free from suspended particles. 5 ml (about 40 drops) of the filtrate are an oral dosage unit composition containing 250 mgm of the active ingredient.

Any one of the other compounds embraced by formula I, a 3H-tautomer thereof, or a non-toxic, pharmacologically acceptable acid addition salt thereof may be substituted for the particular active ingredient in Examples 11 through 15. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

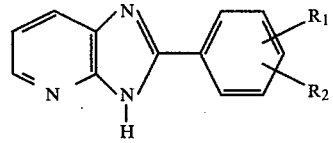

wherein $R_1$ is alkoxy of 1 to 3 carbon atoms; and $R_2$ is (aralkylsulfinyl of 7 to 9 carbon atoms)-(alkoxy of 2 to 3 carbon atoms); or (unsubstituted, mono-, di- or trisubstituted phenylsulfinyl)-(alkoxy of 2 to 3 carbon atoms), where the substituents are attached to the phenyl moiety and are nitro, alkyl of 1 to 3 carbon atoms, alkoxy of 1 to 3 carbon atoms or halogen;

a 3H-tautomer thereof; or a non-toxic, pharmacologically acceptable acid addition salt thereof.

2. A compound of claim 1 where $R_1$ is methoxy, and $R_2$ is —O—CH$_2$—CH$_2$—X, where X is benzylsulfinyl, phenylsulfinyl, chlorophenylsulfinyl, methylphenylsulfinyl, nitrophenylsulfinyl, methoxyphenylsulfinyl, dimethoxyphenylsulfinyl or dimethoxymethylphenylsulfinyl, a 3H-tautomer thereof, or a non-toxic, pharmacologically acceptable acid addition salt thereof.

3. A compound of claim 2, where $R_1$ is in 4-position and $R_2$ is in 2-position on the phenyl ring.

4. A compound of claim 1, which is 2-[2-(2-phenylsulfinyl-ethoxy)-4-methoxyphenyl]-imidazo-[4,5-b]pyridine or a non-toxic, pharmacologically acceptable acid addition salt thereof.

5. A compound of claim 1, which is 2-{2-[2-(4-chlorophenylsulfinyl)-ethoxy]-4-methoxyphenyl}imidazo[4,5-b]pyridine or a non-toxic, pharmacologically acceptable acid addition salt thereof.

6. A compound of claim 1, which is 2-{2-[2-(4-methylphenylsulfinyl)-ethoxy]-4-methoxyphenyl}-imidazo[4,5-b]pyridine or a non-toxic, pharmacologically acceptable acid addition salt thereof.

7. A compound of claim 1, which is 2-{2-[2-(2-methyl-4,5-dimethoxyphenylsulfinyl)-ethoxy]-4-methoxyphenyl}imidazo[4,5-b]pyridine or a non-toxic, pharmacologically acceptable acid addition salt thereof.

8. A hypertensive or cardiotonic pharmaceutical composition consisting essentially of an inert pharmaceutical carrier and an effective hypertensive or cardiotonic amount of a compound of claim 1.

9. The method of raising the blood pressure or increasing the strength of heart muscle contraction in a warm-blooded animal in need thereof, which comprises perorally, parenterally or rectally administering to said animal an effective hypertensive or positively inotropic amount of a compound of claim 1.

* * * * *

UNITED STATES PATENT AND TRADEMARK OFFICE
CERTIFICATE OF CORRECTION

PATENT NO. : 4,327,100
DATED : April 27, 1982
INVENTOR(S) : VOLKHARD AUSTEL ET AL.

It is certified that error appears in the above—identified patent and that said Letters Patent is hereby corrected as shown below:

Title page [54]; and Column 1, line 1: In the title "(4,5-B)" should read -- [4,5-b] --.

Column 1, line 5: "phenyl-" should read -- phenyl)- --.

Column 1, line 6: Delete ")".

Column 3, line 63: "methoxyphenyl-" should read -- methoxyphenyl]- --.

line 64: Delete "]".

Column 4, lines 17 and 36; Column 5, line 41: "ethox-" should read -- ethoxy]- --.

Column 4, lines 18 and 37; Column 5, line 42: Delete "y]-".

Column 6, line 52: "PC 360 A" should read -- PC 350 A --.

Column 8, line 10: "2-[2-(Phenylsulfinyl-" should read -- 2-[2-(2-Phenylsulfinyl- --.

Signed and Sealed this

Fourteenth Day of September 1982

[SEAL]

Attest:

GERALD J. MOSSINGHOFF

Attesting Officer      Commissioner of Patents and Trademarks